United States Patent [19]

Powell

[11] 4,200,639
[45] Apr. 29, 1980

[54] SESBANINE AND THE USE THEREOF IN TREATING LEUKEMIC TUMORS

[75] Inventor: Richard G. Powell, Peoria, Ill.

[73] Assignee: The United States of America as represented by the Secretary of Agriculture, Washington, D.C.

[21] Appl. No.: 25,131

[22] Filed: Mar. 29, 1979

[51] Int. Cl.² .................. A61K 31/445; C07D 471/10
[52] U.S. Cl. ........................................ 424/256; 546/18
[58] Field of Search .................. 546/18; 424/267, 256

[56] References Cited

U.S. PATENT DOCUMENTS

| | | | |
|---|---|---|---|
| 3,406,175 | 10/1968 | Lesher | 546/18 |
| 3,649,635 | 3/1972 | Von Strandtmann et al. | 546/18 |
| 3,936,459 | 2/1976 | Kato et al. | 546/18 |
| 3,947,451 | 3/1976 | Jonsson et al. | 546/18 |

OTHER PUBLICATIONS

*Dorland's Illustrated Medical Dictionary*, 25th Ed., W. B. Saunders, Philadelphia, pp. 896–897 and 1024.
Durant, J., et al., *The Chronic Leukemias*, Chas. C. Thomas, Springfield, Ill., 1972, pp. 54–57.
Geran, R., et al., *Cancer Chemotherapy Reports*, Part 3, vol. 3, No. 2, Sep. 1972, pp. 1–9.
Kingsbury, J., *Poisonous Plants Of The United States And Canada*, Prentice Hall, Englewood Cliffs, N.J., 1964, pp. 353–357.
Robey, A., *Isolation Of The Toxin In Daubentonia Longifolia*, Thesis, Texas A and M Coll. (1925).
Powell, R., et al., *Planta Med.* 1976, 30(1), 1–8.

*Primary Examiner*—John M. Ford
*Assistant Examiner*—Richard A. Schwartz
*Attorney, Agent, or Firm*—M. Howard Silverstein; David G. McConnell; Curtis P. Ribando

[57] ABSTRACT

A novel alkaloid compound named "sesbanine" has been produced from the tissue of a leguminous plant known as *Sesbania drummondii*. Sesbanine has proven to be effective in causing the remission of leukemic tumors in animals and is characterized by the following structural formula:

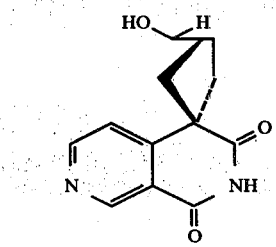

4 Claims, No Drawings

SESBANINE AND THE USE THEREOF IN TREATING LEUKEMIC TUMORS

BACKGROUND OF THE INVENTION

1. Field of the Invention

This invention relates to a novel alkaloid compound which is useful as a chemotherapeutic agent for the remission of leukemia in animals.

2. Description of the Prior Art

A number of leguminous plants belonging to the genus Sesbania have been traditionally used as livestock feeds. However, other members of this genus are notorious for the toxicity of their seeds. These species, including *S. vesicaria*, *S. punicea*, and *S. drummondii*, have been linked to the poisoning of the livestock and poultry in the Southern Coastal Plain of the United States [J. M. Kingsbury, Poisonous Plants of the United States and Canada (1964), pp. 353-357]. Efforts to identify the toxic principle in these species have led to isolation of a variety of saponins and sapogenins, no single one of which has been documented as being toxic. A sapotoxin isolated from *S. drummondii* (*Daubentonia longifolia*) has been reported as a contributing factor [A. Robey, "Isolation of the Toxin of *Daubentonia longifolia*," Thesis, Texas A&M Coll. (1925)].

In a search for chemical compounds which are chemotherapeutically active against leukemia systems, the three toxic species of Sesbania named above were screened by Powell et al. [Planta Medica 30(1): 1-8 (Aug. 1976)]. For each plant, an ethanolic seed extract tested positive against lymphocytic leukemia P388 (PS) in mice. Certain enriched fractions were obtained from the seed extract of *S. vesicaria*, but the responsible agent or agents were never isolated, identified, or obtained in a therapeutically acceptable form.

SUMMARY OF THE INVENTION

I have now surprisingly discovered in seed tissue of *Sesbania drummondii* a novel alkaloid compound which demonstrates potent activity against leukemia in animals, and has been given the name "sesbanine." The compound has been isolated in a pure, crystalline and therapeutically acceptable form, free of interfering toxic agents. It incorporates a previously unreported spirocyclic structure based on a 2,7-naphthyridine nucleus and is characterized by the following formula:

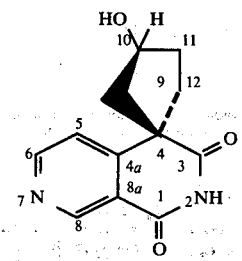

The IUPAC name is trans-3-hydroxyspiro[cyclopentane-1,4'(1'H)[2,7]naphthyridine]-1',3'(2'H)-dione.

In accordance with this discovery, it is an object of the invention to introduce sesbanine as a novel chemical compound having activity against leukemia.

Another object of this invention is to isolate sesbanine in substantially pure form from *S. drummondii* seed material.

It is also an object of the invention to administer the novel alkaloid compound to animals in order to cause remission of leukemia therein.

Other objects and advantages of the invention will become readily apparent from the ensuring description.

DETAILED DESCRIPTION OF THE INVENTION

As mentioned above, the starting material for use in this invention is the seed of *S. drummondii*. This plant species has also been classified under the synonomous names *Daubentonia longifolia* DC and *Daubentonia drummondii* as described in further detail by Kingsbury, supra.

The seed material is prepared for extraction by grinding it in a conventional mill to a suitable particle size in the range of about 0.1-3 mm. in diameter, and generally in the range of 0.5-2 mm. The ground material is then extracted with a polar solvent such as an alcohol, preferably 95% ethanol. The solvent extract is separated from the solid residue and is concentrated to a thin syrup. After dilution with water, the syrup is extracted with an immiscible solvent, which is capable of removing the pigments and lipids. Petroleum ether and other nonpolar solvents are suitable for this purpose. The lipid-free aqueous fraction is then extracted with n-butanol or an equivalent thereof. The butanol phase is recovered from the extraction and constitutes the crude alkaloid extract.

Separation and purification of sesbanine from the crude extract can be effected by the use of the proper combination of conventional techniques including, for example, countercurrent distribution (CCD), column chromatography (CC), liquid chromatography (LC), and high-pressure liquid chromatography (HPLC). I have successfully employed a sequence of operations comprising: (1) 10-unit CCD; (2) $Na_2CO_3$ extraction for removal of phenolics; (3) CC on silica; (4) gel filtration CC with a bead-formed dextran gel for molecular size separation; (5) LC on a coarse-grade, reverse-phase porous silica; and finally (6) LC on a fine-grade, reverse-phase porous silica. While not desiring to be limited thereto, the details of the separation procedure are illustrated by the following example.

EXAMPLE 1

Isolation of SesBanine

Approximately 454 kg. of *S. drummondii* seed material were ground in a Fitz mill to a particle size of about 0.5-2 mm. in diameter. The ground material was placed in a 2270-l. fermentation tank with 908 l. of 95% ethanol, heated to 50° C., and stirred overnight. The ethanol extract was removed and the seed material was similarly extracted four more times, each with about 454 l. of 95% ethanol. The five extracts were combined and concentrated in a vacuum evaporator to a light syrup. A small portion was taken to dryness and labled as Sample F064, and the remainder was diluted with water to yield about 227 l. of an aqueous-ethanol (1:3) extract. The extract was washed three times with petroleum ether and concentrated to remove most of the ethanol. The remaining 45 l. of aqueous extract were taken up in an equal volume of water and then extracted once with 90 l. of n-butanol and twice with 45 l. of n-butanol. The butanol solubles were concentrated in an evaporator to near dryness. This crude alkaloid extract weighed 6.7 kg. and was labled F066.

6.6 kg. of the extract were then passed through a 10-carboy CCD, each carboy containing 16 l. of a three-component biphasic solvent comprising water, ethyl acetate, and methanol in a 2:2:1 ratio, respectively, and adjusted to equal phase volumes. Of 10 fractions collected, numbers 4 (455 g.), 5 (453 g.), and 6 (513 g.) contained the most activity. These were labeled F081, F082, and F083, respectively. 273 g. of Sample F083 were partitioned to remove the polyphenolics by dissolving it in 9 l. of 5% $Na_2CO_3$ solution and extracting it four times with 3–4 l. of ethyl acetate. The extracts were evaporated to dryness, and the residual solids were recovered for a total sample weighing 52 g. which was labeled F164.

This sample was divided into five 10–11 g. portions, each dissolved in a small quantity of chloroform. Each portion was passed through a silica column (6 cm. ID) packed with approximately 250 g. of silica prepared with cloroform. The eluting solvents included 1.5 l. $CHCl_3$-EtOAc (1:1), 1.5 l. EtOAc, 1.5 l. EtOAc-MeOH (1:1), and 0.75 l. MeOH, respectively. Forty 100-ml. fractions collected from each run were combined into four, and similar fractions from the five runs were also combined. Composite fraction 3 (5.9 g.) representing collected fractions 18–32 was determined to be the most active. It was labeled F168.

5.5 g. of F168 were slurried with 20 ml. of water and passed through a polymer column (3.5 cm. ID) packed with 100 g. of "Sephadex G-10" (bead-formed dextran gel, 40–120µ particle size) prepared with water. Twenty 50-ml. fractions were collected by elution with 1 l. of water, and then one 500-ml. fraction by elution with $EtOH-H_2O$ (1:1), and finally a 500-ml. fraction by elution with 95% EtOH. Fractions 1–4 (432.8 mg.) combined into F175, and 5–10 (217.8 mg.) combined into F176 were the most active.

F175 and F176 were each filtered through silica with about 4 ml. MeOH and then separated by reverse-phase liquid chromatography on a column (2 m.×1 cm.) packed with "Bondapak $C_{18}$/Porasil B" (fully porous silica with bonded layer of octadecylsilane, 37–75µ particle size) and using a $H_2O$-MeOH (4:1) solvent at a 9 ml./min. flow rate. Fractions 3–5 (13–63 min.) from F175 showed activity and were labeled F187–F189. Fractions 2–4 (22–75 min.) from F176 showed activity and were labeled F182–F184.

Fractions F182, F184, F187, F188, and F189 were combined and filtered. The resulting 146-g. sample was separated by preparative liquid chromatography on a reverse-phase column (30 cm.×7.9 mm.) packed with "µ Bondapak $C_{18}$" (small-particle silica with bonded layer of octadecylsilane, 10µ particle size) using a $H_2O$-MeOH (4:1) solvent at a flow rate of 2 ml./min. Six fractions were collected. Fraction 2 (16.0 mg.) which came off between 20 and 25 min. contained the most activity and was labeled F204.

F204 was again separated by preparative LC on a reverse-phase $C_{18}µ$ Bondapak column (30 cm.×7.9 mm.) using a $H_2O$-MeOH (9:1) solvent at a flow rate of 2 ml./min. Again six fractions were collected. Fraction 4 (2.8 mg.) which came off between 65 and 73 min. was the most active and was recovered from the column as a pure solid. It was labeled F248.

Pure crystalline solids were also obtained from fractions F081 and F082 by treatments similar to that of F083. All these solids were identified as being the same compound, which was given the name "sesbanine" and was characterized by the following properties: m.p. 240°–243° C. (recrystallized from MeOH); $[\alpha]_D^{23} + 14.6°$ (c 0.56, methanol); UV $\lambda_{max}^{MeOH}$ 228 nm (ϵ10,500); CIMS ($CH_4$, reactant gas) indicating an apparent M+1 at m/e 233.0907 consistent with M equal to $C_{12}H_{12}N_2O_3$.

Characterization of Sesbanine Structure

The chemical structure of sesbanine has been ascertained by spectral analysis and single crystal X-ray crystallography. The prevalent signals observed in the infrared, $^1H$ n.m.r. ($CDCl_3$-$CD_3OD$), $^1H$ n.m.r. (DMSO-$d_6$), and $^{13}C$ n.m.r. spectra are shown in Tables I, II, III, and IV, respectively.

In conducting the X-ray analysis, it was observed that the sesbanine crystallized as flat plates in the monoclinic crystal system. Lattice constants measured by centering 15 high-angle reflections were $\underline{a}=8.00$ (3), $\underline{b}=14.665$ (5), $\underline{c}=9.549$ (4) Å, and $\beta=70.69$ (3)°. The systematic absences and known chirality indicated space group $P2_1$. Intensity data were collected on a fully automated four-circle diffractometer using graphite monochromated MoK$\alpha$radiation (0.71069 Å) and a variable speed, 2.5° ω-scan. A total of 2306 unique diffraction maximum with 2θ≦50.0° were collected in this fashion, and after correction for Lorentz, polarization and background effects, 2116 (92%) were judged observed $[F_o \geq 3\sigma (F_o)]$. All crystallographic calculations were done on a Prime 400 computer, which also generated a perspective drawing corresponding to the structure shown above.

Table I

| Infrared Analysis[1] of Sesbanine | |
|---|---|
| Frequency (cm.$^{-1}$) | Chemical bond |
| 3510 | N—H or O—H |
| 3490 | N—H or O—H |
| 1710 | C=O |
| 1690 | C=O |
| 1600 | aromatic |

[1]Sample in KBr.

Table II

| $^1H$ n.m.r. of Sesbanine in $CDCl_3$—$CD_3OD$ (1:1) | | | | |
|---|---|---|---|---|
| Number of protons | Position[1] | δ | Multiplicity | Coupling constant J (Hz) |
| 1 | 8 | 9.26 | d | 1 |
| 1 | 6 | 8.88 | dd | $J_{6,8} = 1$ |
|  |  |  |  | $J_{5,6} = 6$ |
| 1 | 5 | 7.94 | d | $J_{5,6} = 6$ |
| 1 | 10 | 4.74 | m | — |

[1]Protons in other positions appeared in poorly resolved upfield multiplets (δ 1.8–2.5).

Table III

| $^1H$ n.m.r. of Sesbanine in DMSO-$d_6$ | | | | |
|---|---|---|---|---|
| Number of protons | Position[1] | δ | Multiplicity | Coupling constant J (Hz) |
| 2 | 8.6 | 8.5–9.4 | m,br. | — |
| 1 | 5 | 7.85 | d | $J_{5,6} = 6$ |
| 1 | 10 | 4.50 | m | — |
| 1 | 9 | 2.65 | dd (B of ABM) | 7.14 |

[1]The remaining proton in position 9 and the protons in positions 11 and 12 appeared as a broad upfield multiplet (δ 1.7–2.8).

Table IV

¹³C n.m.r. of Sesbanine

| Position | δ In DMSO—d₆ | δ¹ In pyridine—d₅ |
|---|---|---|
| 1 | 177.2 | 178.5 (s) |
| 3 | 163.8 | 165.0 (s) |
| 4 | 52.1 | 53.2 (s) |
| 4a | 155.8 | 156.6 (s) |
| 5 | 121.7² | —³ |
| 6 | 148.3 | —³ |
| 8 | 153.9 | 154.4 (d) |
| 8a | 121.7² | —³ |
| 9 | 48.5 | 49.7 (t) |
| 10 | 72.7 | 73.9 (d) |
| 11 | 36.1 | 37.8 (t) |
| 12 | 42.4 | 42.9 (t) |

¹Multiplicities of signals were determined by partial decoupling.
²Overlapping signals.
³Signal obscured by solvent peaks.

Chemotherapeutic Activity

The chemotherapeutic activities of the fractions obtained in the isolation procedure may be determined by a KB Cell Culture Screen in accordance with the National Cancer Institute Protocol 1.600 [Geran et al., Cancer Chemother. Rep., Part 3, 3:17 (1972)]. The results of this procedure are expressed as the dose that inhibits growth to 50% of control growth by 3 days after drug addition. Such a dose is referred to as ED 50 and activity is indicated for ED 50 levels of $\leq 30$ µg./ml. The smaller the ED 50 level, the more active the test material. The activities of the fractions obtained in Example 1 beginning with the CCD step are reported below in Table V.

Table V

KB Activities for Example 1 Fractions

| Fraction | ED 50 (µg./ml.) |
|---|---|
| F081 | $8.7 \times 10^{-1}$ |
| F082 | $1.3 \times 10^{0}$ |
| F083 | $1.5 \times 10^{0}$ |
| F164 | $1.4 \times 10^{1}$ |
| F168 | $2.0 \times 10^{0}$ |
| F175 | $3.0 \times 10^{-1}$ |
| F176 | $6.7 \times 10^{-1}$ |
| F182 | $1.4 \times 10^{-1}$ |
| F184 | $7.4 \times 10^{-1}$ |
| F187 | $2.7 \times 10^{-2}$ |
| F188 | $1.9 \times 10^{-1}$ |
| F189 | $8.2 \times 10^{-1}$ |
| F204 | $2.4 \; 10^{-2}$ |
| F248 | $4.7 \times 10^{-2}$ |

The effectiveness of alkaloid compounds against lymphocytic leukemia cells of the strain P388 (PS tumors) implanted in mice is another method of determining activity. These assays are made according to the National Cancer Institute Protocol 1.200 described in Geran et al. referred to above. The usefulness of sesbanine as an antileukemic agent was ascertained by assaying fractions F064–F083 from Example 1 by this procedure. Starting 24 hr. after the tumor implantation, previously determined dosages of each compound were injected intraperitoneally once a day for 9 days. Survival time of treated leukemic mice is compared to that of untreated leukemic mice (T/C×100). A T/C value of 100% indicated no activity. A T/C value greater than 100% means that the treated mice are surviving longer than the control mice. A comound giving a T/C value greater than 125% is indicative of activity as defined by the NCI Protocols, above. The results are shown in Table VI.

Table VI

P388 Activity for Example 1 Fractions

| Fraction | MED¹ (mg./kg.l inj.)²,³,⁴ | T/C of MED¹ (%) | Dose at maximum T/C (mg./kg.l inj.)⁶,³,⁴ | Maximum T/C⁵ (%) |
|---|---|---|---|---|
| F064 | 10.0 | 131 | 45.0 | 175 |
| F066 | 5.0 | 131 | 10.0 | 153 |
| F081 | 0.82 | 132 | 1.25 | 149 |
| F082 | 0.55 | 126 | 0.82 | 150 |
| F083 | 0.55 | 135 | 10.0 | 250 |

¹MED = minimum effective dose,
²All mice were male, CD₂F₁.
³The injection vehicle was saline.
⁴One intraperitoneal injection per day for 9 days.
⁵T/C = mean survival time of test animals/mean survival time of control animals; 125% or above considered active.
⁶Mice for F064 were female, DBA/2; remaining mice were male, CD₂F₁.

Limited sample quantity precluded assay of fractions F164–F248 by this technique, but their activity against leukemic systems is predictable from the KB result shown in Table V.

The terms "effective amount" and "effective dose" as referring to the treatment of animals are defined herein to mean those quantities of alkaloid which will promote remission of leukemia in the animal to which it is administered, without imparting a toxic response. The effective amount may vary with the injection vehicle, the injection schedule, the strain of leukemia, and othe related factors, all of which may be varied without departing from the scope or operativeness of the invention. Generally an effective dose would be in the range of about 0.25–10.0 mg./kg. of body weight/day, and preferably in the range of about 0.5–5.0 mg./kg. of body weight/day. Any pharmaceutically acceptable vehicle or carrier may be used in conjunction with the sesbanine.

It is understood that the foregoing detailed description is given merely by way of illustration and that modification and variations may be made therein without departing from the spirit and scope of the invention.

I claim:

1. A substantially pure chemotherapeutically active alkaloid compound sesbanine having the following structure:

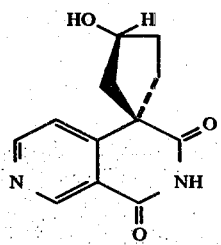

2. A chemotherapeutic composition suitable for the remission of leukemia comprising a pharmaceutically acceptable vehicle and an amount of substantially pure sesbanine effective to promote said remission.

3. The chemotherapeutic composition described in claim 2 wherein said vehicle is an injectable liquid.

4. A method of treating animals for remission of leukemia of the strain P388 comprising administering by injection to said animals a chemotherapeutic composition comprising a pharmaceutically acceptable vehicle and an amount of substantially pure sesbanine effective to promote said remission.

* * * * *